(12) United States Patent
Davies et al.

(10) Patent No.: US 9,078,764 B2
(45) Date of Patent: Jul. 14, 2015

(54) STOMA CLOSURE

(75) Inventors: Geraint Davies, Cambridge (GB); John Cline, New Brunswick, NJ (US); Christopher Gregory, Newtown, PA (US); Alan Cucknell, Cambridge (GB); Julian Scarfe, Cambridge (GB); Pete Cauwood, Cambridge (GB)

(73) Assignee: JPMorgan Chase Bank, N.A., Houston, TX (US)

( * ) Notice: Subject to any disclaimer, the term of this patent is extended or adjusted under 35 U.S.C. 154(b) by 956 days.

(21) Appl. No.: 12/450,717

(22) PCT Filed: Apr. 8, 2008

(86) PCT No.: PCT/US2008/059625
§ 371 (c)(1),
(2), (4) Date: Oct. 8, 2009

(87) PCT Pub. No.: WO2008/124715
PCT Pub. Date: Oct. 16, 2008

(65) Prior Publication Data
US 2010/0121291 A1    May 13, 2010

Related U.S. Application Data

(60) Provisional application No. 60/910,722, filed on Apr. 9, 2007.

(51) Int. Cl.
*A61F 5/441* (2006.01)
*A61F 5/445* (2006.01)
*A61F 5/44* (2006.01)

(52) U.S. Cl.
CPC .................. *A61F 5/445* (2013.01); *A61F 5/441* (2013.01); *A61F 5/4407* (2013.01)

(58) Field of Classification Search
CPC .................................. A61F 5/441; A61F 5/445
USPC .................................................... 604/332–345
See application file for complete search history.

(56) References Cited

U.S. PATENT DOCUMENTS

| | | | | |
|---|---|---|---|---|
| 1,561,020 A | * | 11/1925 | Pond | 604/287 |
| 2,544,579 A | * | 3/1951 | Ardner | 604/337 |
| 3,759,260 A | * | 9/1973 | Nolan et al. | 604/333 |
| 3,815,601 A | * | 6/1974 | Schaefer | 604/15 |
| 3,994,298 A | * | 11/1976 | Des Marais | 604/363 |
| 4,209,009 A | * | 6/1980 | Hennig | 600/30 |
| 4,231,369 A | * | 11/1980 | Sorensen et al. | 604/336 |
| 4,232,672 A | * | 11/1980 | Steer et al. | 604/333 |
| 4,239,043 A | * | 12/1980 | Gellert | 604/15 |
| 4,278,088 A | * | 7/1981 | Reeves et al. | 604/368 |
| 4,344,434 A | | 8/1982 | Robertson | |
| 4,406,657 A | * | 9/1983 | Curutchary | 604/328 |
| 4,693,236 A | * | 9/1987 | Leprevost | 600/32 |
| 4,721,508 A | * | 1/1988 | Burton | 604/338 |
| 4,911,699 A | * | 3/1990 | Fenton | 604/333 |

(Continued)

*Primary Examiner* — Melanie Hand
*Assistant Examiner* — Paula L Craig
(74) *Attorney, Agent, or Firm* — Wilson Sonsini Goodrich & Rosati

(57) ABSTRACT

A stoma closure that includes a conformable portion for conforming to an individual's stoma. The conformable portion includes a sack containing particles. The conformable portion may include a gel that may be loose or be at least partly contained in a sack. The conformable portion may include foam. The conformable portion may be configured to permit venting of flatus, while obstructing the passage of liquid/solid stool.

19 Claims, 3 Drawing Sheets

(56) References Cited

U.S. PATENT DOCUMENTS

| | | | |
|---|---|---|---|
| 4,941,869 A | 7/1990 | D'Amico | |
| 4,950,223 A * | 8/1990 | Silvanov | 600/32 |
| 4,979,947 A * | 12/1990 | Berman | 604/369 |
| 4,981,465 A | 1/1991 | Ballan et al. | |
| 5,009,648 A | 4/1991 | Aronoff | |
| 5,116,139 A * | 5/1992 | Young et al. | 383/49 |
| 5,188,623 A * | 2/1993 | Kok et al. | 604/328 |
| 5,252,340 A * | 10/1993 | Honeycutt | 424/489 |
| 5,403,299 A * | 4/1995 | Schneider | 604/332 |
| 5,531,724 A | 7/1996 | Young | |
| 5,643,234 A * | 7/1997 | Lesko | 604/333 |
| 5,942,186 A * | 8/1999 | Sanada et al. | 422/408 |
| 6,395,955 B1 | 5/2002 | Roe | |
| 6,569,081 B1 * | 5/2003 | Nielsen et al. | 600/32 |
| 6,723,079 B2 * | 4/2004 | Cline | 604/337 |
| 8,217,221 B2 * | 7/2012 | Davies et al. | 604/378 |
| 2002/0110689 A1 * | 8/2002 | Hu et al. | 428/375 |
| 2004/0078219 A1 | 4/2004 | Kaylor | |
| 2004/0157734 A1 * | 8/2004 | Mertens et al. | 502/401 |
| 2004/0193122 A1 * | 9/2004 | Cline et al. | 604/332 |
| 2006/0025740 A1 * | 2/2006 | Osborn et al. | 604/385.18 |
| 2006/0058576 A1 * | 3/2006 | Davies et al. | 600/32 |
| 2006/0058577 A1 | 3/2006 | Davies | |
| 2007/0027434 A1 * | 2/2007 | Pedersen et al. | 604/333 |
| 2007/0123832 A1 * | 5/2007 | Cline et al. | 604/335 |
| 2007/0191794 A1 * | 8/2007 | Cline et al. | 604/335 |

* cited by examiner

STOMA CLOSURE

The present application is a national stage entry of PCT Application No. PCT/US08/59625 filed Apr. 8, 2008, which claims the benefit of U.S. Provisional Application No. 60/910,722 filed Apr. 9, 2007.

The present invention relates to the field of stoma closures, for blocking the discharge of effluent from a stoma. A stoma closure may at least partly enter the stoma and/or may at least partly fit against the stoma and/or may at least partly fit around the periphery of the stoma.

BACKGROUND TO THE INVENTION

The creation of an ostomy (stoma) is the therapy for many sufferers of diseases or injury of the gastrointestinal or urinary tract. An ostomy is the rerouting of the tract through the abdominal wall to outside the patient's body. Once a stoma has been created, the patient must, usually for the rest of his or her life, use a device worn on the body for capturing or containing the body waste. This has traditionally been done with a bag or pouch attached to the body with adhesive patches or constricting belts. However, the wearing of such a pouch may be an embarrassing experience for many ostomates. A pouch may require changes in an ostomate's activities.

A stoma closure offers the potential for an ostomate to return to some form of normality. The closure is used to block the stoma, in order to store body waste temporarily inside the tract. The closure is removable manually when the ostomate desires to discharge the body waste.

However, it is difficult to design a stoma closure that can combine user friendliness and patient comfort with a high sealing performance. Seal performance is extremely important, in order to spare the ostomate the leakage of body waste. The seal also has to be able to withstand motion of the body without leaking. Yet, at the same time, the closure should be easy for the ostomate to apply and use, be comfortable to wear, and avoid damage to the highly sensitive stoma tissue.

U.S. Pat. Nos. 4,941,869; 4,981,465; and 4,344,434 describe stoma closures in the form of expanding foam plugs insertable into the stoma. However, it is believed that none of the above devices has enjoyed high patient acceptance, because the devices fail to satisfy the high personal requirements of ostomates as explained above.

SUMMARY OF THE INVENTION

The present invention provides a stoma closure configured to at least partly enter the stoma and/or at least partly fit against the stoma and/or at least partly fit around the periphery of the stoma. The stoma closure comprises a conformable portion.

The stoma closure may, for example, include one or more of the following optional features:
  (a) The conformable portion may comprise a plurality of movable particles contained in a sack. The sack has a porous configuration for allowing body waste to contact and/or enter the sack, while confining the particles captive within the sack.
  (b) The conformable portion may comprise a gel. A majority of the conformable portion may be implemented by the gel. The gel may be loose, or at least partly contained in a sack and/or sleeve. The gel functions as an artificial stool around or through which flatus may pass under peristalsis of the intestine.
  (c) The conformable portion may comprise foam. The foam may include and/or provide one or more flatus vent passages therethrough. Additionally, a surface portion of the foam includes a surface feature (e.g., a channel) to aid passage of flatus around the foam. The foam also prevents the release of solid stool while allowing flatus to be released, and/or while allowing liquid stool to escape and be wicked away from the stoma.

The above features may be used in isolation, or combined, as desired.

Further features and advantages of the invention will be apparent from the following detailed description. Although certain significant features have been described above and in the appended claims, the Applicant claims protection for any novel feature or idea described herein and/or illustrated in the drawings, whether or not emphasis has been placed thereon.

DETAILED DESCRIPTION OF PREFERRED EMBODIMENTS

Figure 1:
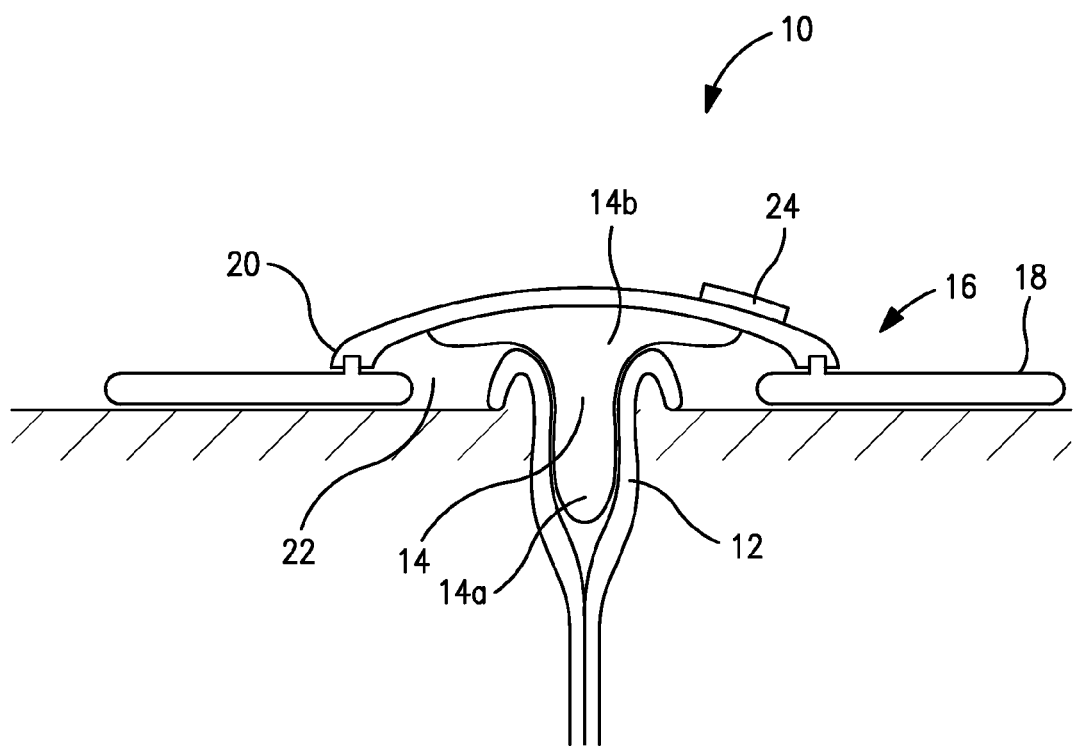
FIG. 1 is a schematic cross sectional view through a stoma closure.

Referring to FIG. 1, a stoma closure 10 is illustrated for blocking the discharge of effluent from a stoma 12. The closure 10 is configured to at least partly enter the stoma 12; at least partly fit against the stoma 12; and/or to at least partly fit around the periphery of the stoma 12. The closure 10 includes a conformable portion 14 that is able to conform at least partly to a size and/or shape of an individual's stoma, in order to achieve a reliable, yet comfortable, seal.

In one form (FIG. 1), the conformable portion 14 comprises a bung or plug 14 for at least partial insertion into a stoma 12. The plug 14 includes a distal end 14a for insertion into the stoma 12, and a proximal end 14b for abutting the stoma mouth. The proximal end 14a includes a rounded or flared shape for abutting against an exterior surface of the stoma 12. In another form (not shown), the conformable portion 14 comprises a pad that fits against the stoma 12, and a portion that fits around the periphery of the stoma 12.

The conformable portion 14 may be loose, but be retained in position generally by frictional engagement with the stoma wall. Additionally, a support 16 retains the conformable portion 14 in position. The support 16 comprises a support belt or garment worn on the body, and/or an attachment device that attaches to the skin. In the illustrated form, the support 16 comprises an adhesive pad 18, and a mounting member 20 mounting and/or retaining the conformable portion 14 relative to the adhesive pad 18. The mounting member 20 completely contains (e.g., covers) the conformable portion 14 and a region 22 around the stoma 12, or the mounting member 20 may be partly open. The conformable portion 14 is attached to the mounting member 20, or may be retained loosely by the mounting member 20. The support 16 comprises a deodorizing filter 24 for filtering flatus venting from the stoma through, or around, the conformable portion 14. For example, the deodorizing filter may comprise activated or non-activated charcoal or other odor counteractant material.

Figure 2:
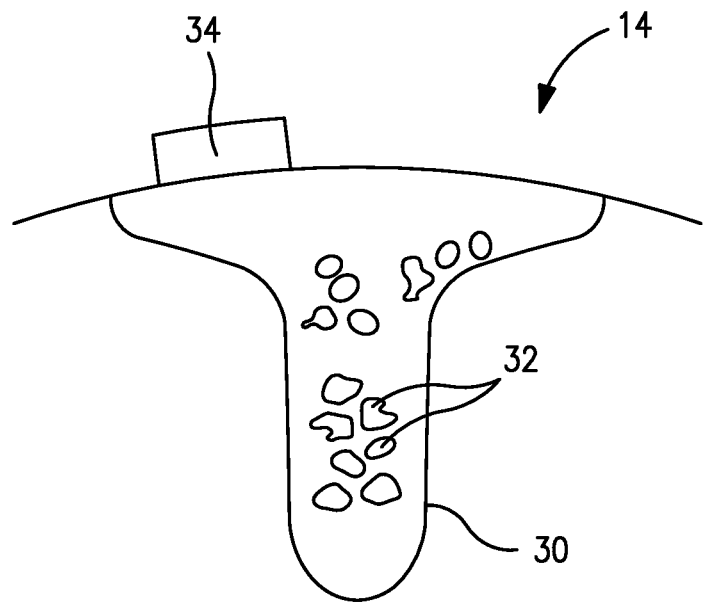
FIG. 2 is a schematic cross sectional view of an example of conformable portion of the stoma closure.

Referring to FIG. 2, the conformable portion 14 comprises a sack and/or sleeve 30 containing a plurality of particles 32. Each of the particles 32 are in a size range between about 0.1 mm and about 10 mm (inclusive). The size refers to a diameter or other dimension (e.g., lateral dimension) of the particle 32. The particles 32 may be of substantially the same size (e.g., to within about 10% of an average size), or the particles 32 may be of different sizes. The particles 32 may be of substantially the same (or at least similar) shape, or the particles 32 may be of different shapes.

The sack 30 and particles 32 are effective to block the flow of stool. The particles 32 are able to move relative to each other inside the sack 30. Such movement enables the conformable portion 14 to conform to the shape of the stoma 12 without exerting a significant pressure on the stomal tissue. Too great a pressure may cause damage to the stomal tissue, and may also be uncomfortable for the ostomate.

The physical characteristics of the conformable portion 14 are governed by one or more characteristics of the sack 30 and/or the particles 32. For example, such physical characteristics may include one or more of:
 conformability;
 responsiveness to movement;
 stiffness; and/or
 porosity to fluid.
Such physical characteristics are affected, or controlled, by one or more of:
 size(s) of the particles 32;
 shape(s) of the particles 32;
 mix of different particle 32 sizes and/or shapes;
 order in which the particles 32 are packed inside the sack 30;
 space available inside the sack 30;
 profile of the sack 30 (e.g., the sack 30 may be profiled to be less conformable in a relatively narrow portion, and more conformable in a relatively wide portion);
 material from which the sack 30 is made (for example, such material may be a fluid impermeable membrane or a fluid permeable membrane; a mesh or net having apertures smaller than the size(s) of the particles 32 which enables fluid to penetrate the sack 30, but act as a blockage for stool);
 materials from which the particles 32 are made (for example, the particles 32 could be rigid, plastically conformable, elastically conformable, or porous, or a combination of these or other attributes that could be employed to improve or control functional properties);
 surface characteristics of the particles 32 (for example, the particles 32 may be hydrophilic, coated with a hydrophillic surface treatment, hydrophobic, coated with a hydrophobic surface treatment or other surface treatments of the particles.
 control strings (not shown) embedded within the sack 30 to at least partly constrain the shape or size of the sack 30;
 control relative movement of the particles, for example, by mounting a plurality of the particles on a string or thread (not shown;
 one or more internal sacks (not shown) nested or contained within an outer sack 30 (for example, the internal sack(s) may provide different physical properties and/or may contain different particles from the outer sack 30);
 some particles 32 are fused together to form compound shapes (for example, such shapes may have different frictional properties from the unfused particle shapes); and/or
 some particles 32 are attached to the inner wall of the sack 30 to modify or control how it conforms to the surface of the bowel.

In one form (see FIG. 2), a pressurization and/or depressurization device 34 is provided for inflating and/or deflating the sack 30. In such a case, the sack 30 is made of a material that is impermeable to a pressurization fluid used. For example, the pressurization fluid may be a gas (e.g., air) or a liquid (e.g., saline). The pressurization and/or depressurization device 34 may be a pump. Pressurization of the sack 30 increases the internal volume of the sack 30, and allows the particles 32 to move more freely relative to each other. Pressurization increases the conformability of the conformable portion 14. Depressurization of the sack 30 decreases the internal volume of the sack 30, and thereby increases the frictional forces between the particles 32. Depressurization of the sack 30 decreases the conformability of the conformable portion 14.

The pressurization and/or depressurization device 34 may be carried on the supporter may be remote from the support. The pressurization and/or depressurization device 34 includes a pump detachably connectable to the conformable member 14. The pressurization and/or depressurization device 34 includes a valve.

In a slightly modified version of the above, the sack 30 is made of an elastic material. In a normal state, the elastic material squeezes the particles 32 to lock the particles 32 together (e.g., without additional depressurization). The pressurization and/or depressurization device 34 inflates the sack 30 to increase the conformability. When the pressure is relieved, the elastic material of the sack 30 squeezes the particles 32 to reduce the conformability.

Alternatively, the sack 30 may be capable of being altered by the ostomate or health care professional to optimize the fit inside the stoma 12. This is done, for example, by providing a means of temporarily opening the sack 30 for removal, addition, or replacement of particles 32.

The particles 32 may interact with body waste (e.g., solid stool, liquid stool and/or flatus) passing through the sack 30 and/or contacting the sack 30. For example, the particles 32 may include a malodor counteractant for avoiding unpleasant odors. The malodor counteractant may, for example, include one or more of an odor absorbent, an odorous gas reactant, and a pleasant masking fragrance. Additionally, the particles 32 may include a liquid absorbent. The liquid absorbent may, for example, be a superabsorbent. The particles 32 may expand when wet. The particles 32 may function to obstruct leakage of solid and/or liquid stool through the stoma 12.

Additionally, the conformable portion 14 may comprise or carry a gel. For example, the gel may be coated on the sack 30. The gel may serve as a lubricant to aid insertion of the conformable portion 14 into the stoma 12. Additionally, the gel may act as a sealing medium between the sack 30 and the stomal tissue.

Figure 3:
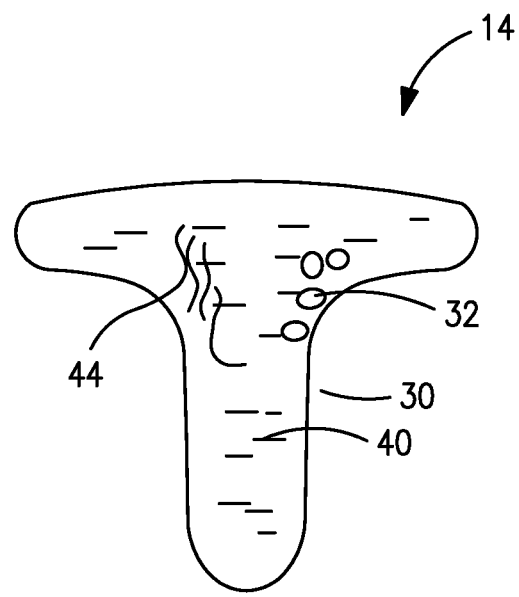
FIG. 3 is a schematic cross sectional view of an additional example of conformable portion of the stoma closure.

Referring to FIG. 3, a gel 40 constitutes at least a majority of the conformable portion 14. The gel 40 is enclosed within a sack and/or sleeve 30. The sack 30 allows the gel 40 to conform to different sizes and shapes of stoma 12, but substantially confines the gel 40. The sack 30 is impermeable to the gel 40 to prevent migration of the gel 40, or the sack 30 may allow some migration of the gel 40. Alternatively, the gel 40 may be used loosely without a confining sack 30.

The gel 40 functions as an artificial stool located at the stoma 12. A normal intestine/rectum allows flatus to pass around stool by a process of peristalsis without passing the stool. The gel 40, acting as an artificial stool, at least partly enables a similar bodily function to allow flatus to pass through or around the gel by peristaltic action, while obstructing solid and/or liquid stool flow. The gel 40 is sufficiently viscous to prevent it from running out of the stoma 12 and to resist the peristalsis in the stoma 12. The gel 40 is restrained by a support 16 as described above, or the gel 40 may be loose.

The gel 40 may be colored to aid easy consumer use. A colored gel 40 may also be useful in identifying a leakage from the stoma 12. The gel 40 may be extruded to appear at the skin surface before any liquid and/or solid body waste leaks. The potential for a leak of stool may therefore be identified before the leak takes place. Alternatively, the gel 40 may be configured to change color when contacted by solid stool and/or liquid stool and/or flatus. The color may be chosen to help the ostomate feel more at ease, to allow for easier viewing of the stool under poor lighting.

Properties of the gel 40 are controlled by mixing one or more additives into the gel 40. The properties include physical properties, such as viscosity. For example, fibers 44 and/or particles 32 may be added to the gel 40 to create a mixture having desired properties.

The gel 40 is inert. Alternatively, the gel 40 may comprise one or more active ingredients, for example, a detergent and/or a cleaning aid and/or an antibacterial agent.

Figure 4:
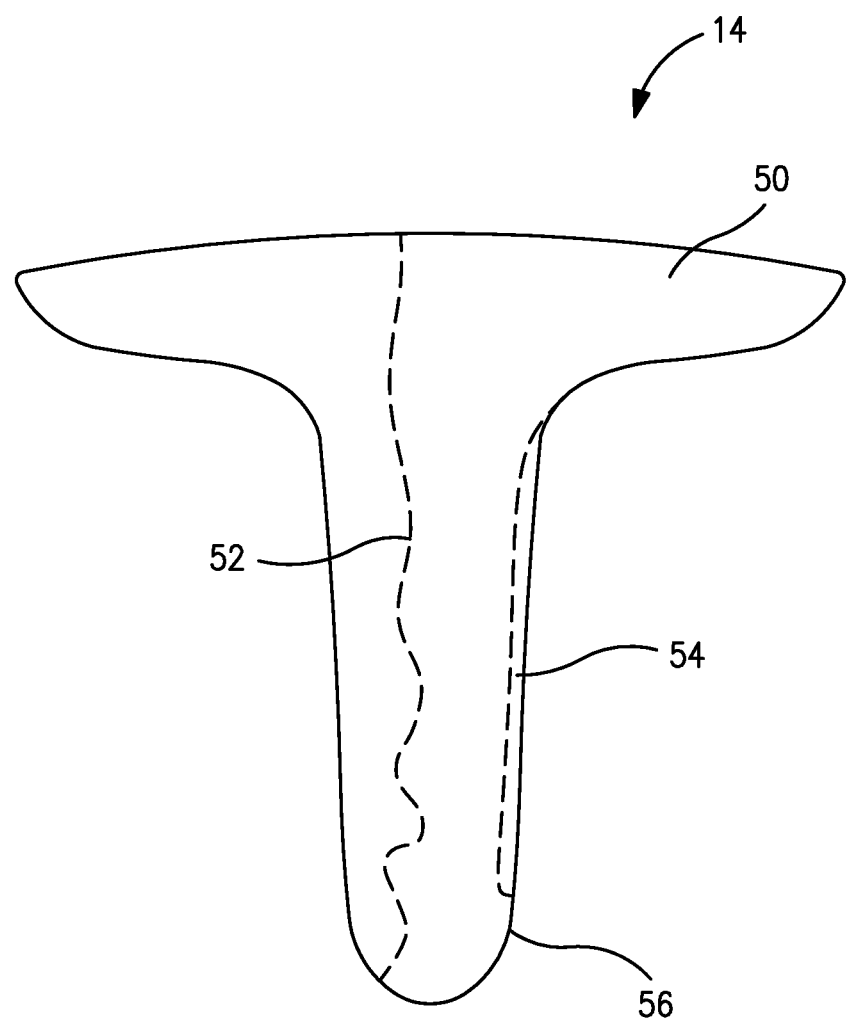
FIG. 4 is a schematic cross sectional view of another additional example of conformable portion of the stoma closure.

Referring to FIG. 4, as an alternative to the above forms of the conformable portion 14, the conformable portion 14 may comprise a foam material 50. The foam material 50 may be a visco-elastic material, or a plastically-deformable material. The nature of the foam material 50 enables the conformable portion to conform to different shapes and sizes of stoma 12. The foam material 50 may be closed on its proximal end, but could be completely open at its distal end.

The foam material 50 may be open-cell and/or closed-cell. One or more channels 52 in the foam material 50 enables flatus to pass through the foam. Only one channel 52 is illustrated in FIG. 4 for the sake of brevity, although multiple (e.g., interconnected) channels 52 may extend throughout the foam material 50. The channels 52 may have a tortuous and/or narrow path. The tortuous and/or narrow path enables flatus to pass through relatively easily, but obstruct the passage of liquid and/or solid stool. The cell-like nature of the foam material 50 provides excellent separation of flatus from liquid, and retains the liquid captive in the foam material 50.

Additionally, the foam material 50 may include one or more surface features 54 formed in an external surface 56 thereof. The surface features 54 comprise one or more channels 52, valleys and/or ridges to enable flatus to flow around the foam material 50 as it does for stool under the effects of natural peristalsis of the intestine.

Although certain features have been described above as alternatives or in isolation, it will be appreciated that any of the above features may be combined as desired. For example, the gel 40 may be used with the foam material 50, to provide additional sealing and/or lubrication.

The foregoing description is merely illustrative of preferred embodiments of the invention. Many modifications, improvements and equivalents may be used within the scope and/or spirit of the invention.

The invention claimed is:

1. A stoma closure comprising:
   a. a mounting member for attachment directly or indirectly to skin around the stoma,
   b. a flexible chamber secured to said mounting member,
   c. a plurality of particles contained inside the flexible chamber, said flexible chamber and said particles being conformable to the stoma so as to block the passing of stool from the stoma, wherein said particles are configured to freely move inside of said flexible chamber, and wherein said flexible chamber confines said particles entirely inside said flexible chamber,
   d. a deodorizing filter secured to said mounting member for filtering flatus venting from the stoma through or around said flexible chamber and through said mounting member.

2. The stoma closure according to claim 1, wherein the flexible chamber is impermeable to liquid stool.

3. The stoma closure according to claim 1, wherein the flexible chamber is porous.

4. The stoma closure according to claim 1, wherein the flexible chamber comprises a mesh material.

5. The stoma closure according to claim 1, wherein the particles are in a size range of from about 0.1 mm to about 10 mm.

6. The stoma closure according to claim 1, wherein the particles are about the same size as one another.

7. The stoma closure according to claim 1, wherein the particles have generally the same shape as one another.

8. The stoma closure according to claim 1, wherein at least some of the particles are of generally different shape from other particles.

9. The stoma closure according to claim 1, wherein at least some of the particles are of generally different size from other particles.

10. The stoma closure according to claim 1, wherein the chamber is pressurizable.

11. The stoma closure according to claim 1, wherein the chamber is depressurizable.

12. The stoma closure according to claim 1, wherein the chamber comprises elastic material.

13. The stoma closure according to claim 1, wherein at least some of the particles comprise malodor counteractant.

14. The stoma closure according to claim 1, wherein at least some of the particles are expandable when wet.

15. The stoma closure according to claim 1, wherein at least some of the particles have a surface characteristic, or a surface treatment, that is hydrophilic.

16. The stoma closure according to claim 1, wherein at least some of the particles have a surface characteristic, or a surface treatment, that is hydrophobic.

17. The stoma closure according to claim 1, wherein at least some of the particles have a surface characteristic or surface treatment that enhances their performance for controlling the release of effluent from a stoma.

18. The stoma closure of claim 1, wherein said chamber comprises a distal end configured to be inserted inside of said stoma and a proximal end comprising a flared shape configured to engage an exteriorized surface of said stoma.

19. The stoma closure of claim 1, further comprising a belt configured to engage with said mounting member and secure said mounting member to the skin of a patient.

* * * * *